US009907498B2

(12) United States Patent
Barrows et al.

(10) Patent No.: US 9,907,498 B2
(45) Date of Patent: Mar. 6, 2018

(54) CHANNEL FORMATION

(71) Applicant: Verily Life Sciences LLC, Mountain View, CA (US)

(72) Inventors: Daniel Patrick Barrows, Sunnyvale, CA (US); James Etzkorn, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 688 days.

(21) Appl. No.: 14/476,916

(22) Filed: Sep. 4, 2014

(65) Prior Publication Data
US 2016/0066825 A1    Mar. 10, 2016

(51) Int. Cl.
*G02C 7/04* (2006.01)
*A61B 5/1477* (2006.01)
(Continued)

(52) U.S. Cl.
CPC ........ *A61B 5/1477* (2013.01); *A61B 5/14532* (2013.01); *A61B 5/6821* (2013.01); *G02B 1/043* (2013.01); *G02C 7/00* (2013.01); *G02C 7/04* (2013.01); *G02C 11/10* (2013.01); *B29C 63/0013* (2013.01); *B29K 2029/00* (2013.01)

(58) Field of Classification Search
CPC ... A61B 5/1477; A61B 5/14532; A61B 5/145; A61B 5/6821; G02C 7/00; G02C 7/04; G02C 11/10; G02B 1/043
USPC ............ 351/159.01, 159.02, 159.03, 159.39; 264/2.3, 1.36
See application file for complete search history.

(56) References Cited

U.S. PATENT DOCUMENTS

| 4,068,933 A | 1/1978 | Seiderman |
| 4,401,371 A | 8/1983 | Neefe |

(Continued)

FOREIGN PATENT DOCUMENTS

| CN | 201017117 | 2/2008 |
| KR | 1020120010551 | 2/2012 |

(Continued)

OTHER PUBLICATIONS

International Search Report and Written Opinion of International Application No. PCT/US2015/048236 dated Dec. 15, 2015 (dated Dec. 16, 2015).

*Primary Examiner* — William R Alexander
(74) *Attorney, Agent, or Firm* — McDonnell Boehnen Hulbert & Berghoff LLP

(57) ABSTRACT

A body-mountable device may be formed of a polymeric material. A molding form can define a cavity and polymeric material can be formed using the mold to create a device shaped in accordance with the cavity. Electronics disposed on a substrate can be encapsulated within the polymeric material by forming a first layer of polymeric material, positioning the substrate on the first layer, and then forming a second layer of polymeric material over the substrate. A channel can expose a sensor disposed on the substrate. The channel may be formed while molding the second layer of polymeric material over the substrate. The molding form can include a protrusion that extends toward the sensor. A sacrificial sealant material can be applied to the sensor or the protrusion to create a seal between the protrusion and the sensor. The polymeric material forms around the sealed protrusion to create the channel.

6 Claims, 8 Drawing Sheets

(51) Int. Cl.
*A61B 5/145* (2006.01)
*G02B 1/04* (2006.01)
*G02C 7/00* (2006.01)
*G02C 11/00* (2006.01)
*A61B 5/00* (2006.01)
*B29K 29/00* (2006.01)
*B29C 63/00* (2006.01)

(56) References Cited

U.S. PATENT DOCUMENTS

| | | | |
|---|---|---|---|
| 4,571,039 A | 2/1986 | Poler | |
| 4,909,818 A | 3/1990 | Jones | |
| 5,044,742 A | 9/1991 | Cohen | |
| 5,271,875 A * | 12/1993 | Appleton | B29C 33/0038 249/160 |
| 5,626,865 A | 5/1997 | Harris et al. | |
| 6,036,314 A | 3/2000 | Wolfson | |
| 6,312,393 B1 * | 11/2001 | Abreu | A61B 3/1241 600/558 |
| 7,591,556 B2 | 9/2009 | Rosenthal | |
| 7,731,872 B2 * | 6/2010 | Bruce | B29C 33/202 156/73.1 |
| 7,878,650 B2 | 2/2011 | Fritsch et al. | |
| 7,927,519 B2 * | 4/2011 | Domschke | A61B 5/14532 264/1.31 |
| 8,080,187 B2 * | 12/2011 | Tepedino, Jr. | B29D 11/00009 264/1.32 |
| 8,385,998 B2 | 2/2013 | Zhang et al. | |
| 8,506,740 B2 | 8/2013 | Say | |
| 8,535,043 B2 * | 9/2013 | Perez | B29C 33/303 249/160 |
| 9,307,901 B1 * | 4/2016 | Linhardt | A61B 3/101 |
| 9,332,935 B2 * | 5/2016 | Etzkorn | A61B 5/682 |
| 9,636,016 B1 * | 5/2017 | Etzkorn | A61B 5/00 |
| 9,636,050 B1 | 5/2017 | Etzkorn et al. | |
| 2002/0049389 A1 * | 4/2002 | Abreu | A61B 3/1241 600/558 |
| 2002/0075447 A1 | 6/2002 | Andino et al. | |
| 2002/0193674 A1 * | 12/2002 | Fleischman | A61B 3/16 600/399 |
| 2004/0100704 A1 | 5/2004 | Shadduck | |
| 2004/0181172 A1 | 9/2004 | Carney et al. | |
| 2004/0209973 A1 | 10/2004 | Steffen et al. | |
| 2006/0186564 A1 | 8/2006 | Adams et al. | |
| 2006/0265058 A1 | 11/2006 | Silvestrini et al. | |
| 2006/0290882 A1 | 12/2006 | Meyers et al. | |
| 2007/0153231 A1 | 7/2007 | Iuliano | |
| 2008/0176271 A1 * | 7/2008 | Silver | A61B 5/0031 435/29 |
| 2010/0072643 A1 * | 3/2010 | Pugh | B29D 11/00038 264/2.7 |
| 2010/0076553 A1 * | 3/2010 | Pugh | B29D 11/00038 623/6.22 |
| 2010/0103368 A1 * | 4/2010 | Amirparviz | B29D 11/00826 351/158 |
| 2010/0103369 A1 | 4/2010 | Pugh et al. | |
| 2010/0109175 A1 * | 5/2010 | Pugh | B29D 11/00028 264/1.36 |
| 2010/0110372 A1 * | 5/2010 | Pugh | B29D 11/00009 351/159.75 |
| 2011/0155587 A1 | 6/2011 | Shacham-Diamand et al. | |
| 2012/0162600 A1 * | 6/2012 | Pugh | G02C 7/04 351/159.03 |
| 2012/0199995 A1 * | 8/2012 | Pugh | A61N 5/0618 264/1.36 |
| 2012/0236524 A1 | 9/2012 | Pugh et al. | |
| 2012/0245444 A1 | 9/2012 | Otis et al. | |
| 2013/0135578 A1 | 5/2013 | Pugh et al. | |
| 2013/0161846 A1 | 6/2013 | Goodenough et al. | |
| 2013/0194540 A1 * | 8/2013 | Pugh | A61F 2/1635 351/159.03 |
| 2013/0243655 A1 | 9/2013 | Li et al. | |
| 2013/0258277 A1 * | 10/2013 | Pugh | G02C 7/083 351/159.39 |
| 2013/0284691 A1 * | 10/2013 | Pandojirao-S | B29D 11/00163 216/12 |
| 2013/0308092 A1 | 11/2013 | Groisman | |
| 2014/0002789 A1 | 1/2014 | Pugh et al. | |
| 2014/0005514 A1 * | 1/2014 | Pugh | A61F 9/0017 600/383 |
| 2014/0088381 A1 | 3/2014 | Etzkorn et al. | |
| 2014/0107444 A1 | 4/2014 | Liu | |
| 2014/0107445 A1 | 4/2014 | Liu | |
| 2014/0185010 A1 * | 7/2014 | Bernert | A61B 3/112 351/219 |
| 2014/0192315 A1 | 7/2014 | Liu et al. | |
| 2014/0194706 A1 | 7/2014 | Liu et al. | |
| 2014/0194713 A1 | 7/2014 | Liu | |
| 2014/0200424 A1 | 7/2014 | Etzkorn et al. | |
| 2014/0200425 A1 | 7/2014 | Etzkorn et al. | |
| 2014/0213867 A1 | 7/2014 | Pletcher et al. | |
| 2014/0240655 A1 * | 8/2014 | Pugh | G02C 7/04 351/158 |
| 2014/0240656 A1 * | 8/2014 | Pugh | G02C 7/04 351/159.03 |
| 2014/0315241 A1 * | 10/2014 | Dobson | C12Q 1/04 435/34 |

FOREIGN PATENT DOCUMENTS

| | | |
|---|---|---|
| WO | 2004064629 | 8/2004 |
| WO | WO2014012016 | 1/2014 |

* cited by examiner

CHANNEL FORMATION

BACKGROUND

Unless otherwise indicated herein, the materials described in this section are not prior art to the claims in this application and are not admitted to be prior art by inclusion in this section.

Body-mountable and/or implantable devices may include sensors and other bio-interactive electronics. In some cases such devices may operate using harvested energy from a photovoltaic cell or from a radio frequency antenna. Such electronics may be embedded in biocompatible materials, such as polymeric materials that are shaped to facilitate mounting and/or implantation in the body.

Electrochemical amperometric sensors measure concentrations of an analyte by measuring currents caused by oxidation or reduction reactions of the analyte in the presence of a charged electrode. Generally, a negatively charged electrode donates electrons to the analyte in a reduction reaction where the analyte becomes more negatively charged, whereas a positively charged electrode receives electrons from the analyte in an oxidation (or ionization) reaction where the analyte becomes more positively charged. The charged electrode (or working electrode) induces the reactions and receives or donates electrons to generate a current that provides the output signal. Thus, when the working electrode is appropriately charged, the output current is proportional to the reaction rate, which provides a measure of the concentration of the analyte surrounding the working electrode.

In some examples, an enzyme is fixed proximate the working electrode to selectively react with a desired analyte. For example, glucose oxidase can be fixed near the working electrode to react with glucose and release hydrogen peroxide, which is then electrochemically detected by the working electrode to indicate the presence of glucose. Other enzymes and/or reagents can be used to detect other analytes.

SUMMARY

A body-mountable device may be formed of a polymeric material. A molding form can define a cavity and polymeric material can be formed using the mold to create a device shaped in accordance with the cavity. Electronics disposed on a substrate can be encapsulated within the polymeric material by forming a first layer of polymeric material, positioning the substrate on the first layer, and then forming a second layer of polymeric material over the substrate. A channel can expose a sensor disposed on the substrate. The channel may be formed while molding the second layer of polymeric material over the substrate. The molding form can include a protrusion that extends toward the sensor. A sacrificial sealant material can be applied to the sensor or the protrusion to create a seal between the protrusion and the sensor. The polymeric material forms around the sealed protrusion to create the channel.

Some embodiments of the present disclosure provide a method. The method can include forming a first layer of polymeric material in a first part of a molding form. The molding form can include the first part and a second part configured to engage one another at an interface that defines a boundary of a cavity between the first and second parts. The second part can include a surface that defines a portion of the cavity and a protrusion that extends from the surface. The method can also include positioning a substrate over the first layer of polymeric material. The substrate can have a sensor disposed thereon. The method can also include applying a sacrificial sealant material to at least one of the protrusion or the sensor. The method can also include engaging the second part of the molding form with the first part such that the protrusion contacts the sacrificial sealant material while the sacrificial sealant material contacts the sensor. The sacrificial sealant material can substantially cover the sensor. The method can also include forming a second layer of polymeric material over the substrate and the first layer and around the protrusion while the sacrificial sealant material contacts both the protrusion and the sensor. The second layer of polymeric material and the first layer of polymeric material can combine within the molding form so as to substantially encapsulate the substrate within polymeric material shaped in accordance with the cavity. The method can also include removing the shaped polymeric material from the molding form. The method can also include removing the sacrificial sealant material covering the sensor to thereby expose the sensor. The sensor can be exposed through a channel in the polymeric material. The channel can be at least partially formed by the protrusion.

Some embodiments of the present disclosure provide a system. The system can include a molding form including a first part and a second part configured to engage one another at an interface that defines a boundary of a cavity between the first and second parts. The first part can include a surface that defines a portion of the cavity. The second part can include a surface that defines a portion of the cavity and a protrusion that extends from the surface. The protrusion can be configured to contact a sacrificial sealant material while the sacrificial sealant material contacts a sensor of a body-mountable device that is being formed within the molding form. The body-mountable device can include a channel through which the sensor is exposed. The channel can be at least partially formed by the protrusion.

Some embodiments of the present disclosure provide a body-mountable device. The body-mountable device can include a polymeric material shaped in accordance with a molding form. The molding form can include a first and second part configured to engage one another at an interface that defines a boundary of a cavity between the first and second parts. The second part can include a surface that defines a portion of the cavity and a protrusion that extends from the surface. The body-mountable device can also include a substrate having a sensor disposed thereon. The substrate can be substantially encapsulated within the polymeric material. The sensor can be exposed through a channel in the polymeric material. The channel can be at least partially formed by the protrusion and by a sacrificial sealant material that contacts both the sensor and the protrusion during formation of the body-mountable device.

Some embodiments of the present disclosure provide means for forming a first layer of polymeric material in a first part of a molding form. Some embodiments of the present disclosure provide means for positioning a substrate over the first layer of polymeric material. Some embodiments of the present disclosure provide means for applying a sacrificial sealant material to at least one of the protrusion or the sensor. Some embodiments of the present disclosure provide means for engaging the second part of the molding form with the first part such that the protrusion contacts the sacrificial sealant material while the sacrificial sealant material contacts the sensor. Some embodiments of the present disclosure provide means for forming a second layer of polymeric material over the substrate and the first layer and around the protrusion while the sacrificial sealant material contacts both the protrusion and the sensor. Some embodiments of the present disclosure provide means for removing the shaped polymeric material from the molding form. Some embodiments of the present disclosure provide means for removing the sacrificial sealant material covering the sensor to thereby expose the sensor.

These as well as other aspects, advantages, and alternatives, will become apparent to those of ordinary skill in the art by reading the following detailed description, with reference where appropriate to the accompanying drawings.

DETAILED DESCRIPTION

Figure 1:
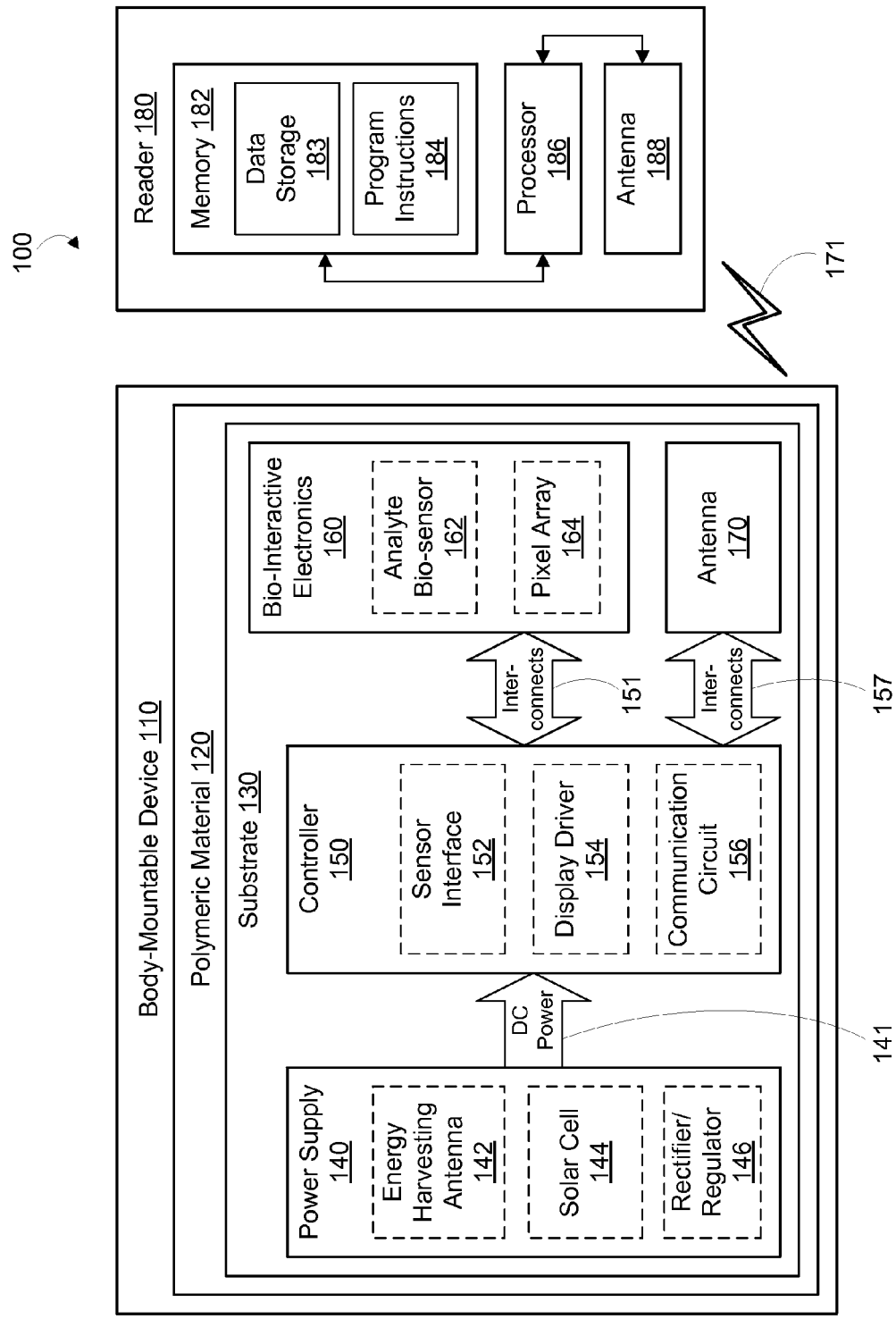
FIG. 1 is a block diagram of a system with a body-mountable device in wireless communication with an external reader, according to an example embodiment.

The following detailed description describes various features and functions of the disclosed methods, apparatus, and systems with reference to the accompanying figures. In the figures, similar symbols typically identify similar components, unless context dictates otherwise. The illustrative method, apparatus, and system embodiments described herein are not meant to be limiting. It will be readily understood that certain aspects of the disclosed methods, apparatus, and systems can be arranged and combined in a wide variety of different configurations, all of which are contemplated herein.

I. Overview

A body-mountable device may be configured to monitor health-related information based on at least one analyte detected in a fluid of a user wearing the body-mountable device. Such a body-mountable device may be formed (e.g., fabricated) in a molding form. The molding form can define a cavity and polymeric material can be formed using the mold to create a device shaped in accordance with the cavity. Electronics disposed on a substrate can be encapsulated within the polymeric material by forming a first layer of polymeric material, positioning the substrate on the first layer, and then forming a second layer of polymeric material over the substrate. A channel in the polymeric material can expose a sensor disposed on the substrate, and the sensor can measure an analyte concentration of fluid that occupies the channel. The channel may be formed while molding the second layer of polymeric material over the substrate. The molding form can include a protrusion that extends toward the sensor. A sacrificial sealant material can be applied to the sensor or the protrusion to create a seal between the protrusion and the sensor. The polymeric material forms around the sealed protrusion to create the channel.

The body-mountable device may be an eye-mountable device formed from polymeric material in a two-part mold. The mold can include a first part that defines a posterior surface of an eye-mountable device and a second part that defines an anterior surface. In use, the posterior surface can be contact-mounted against an eye surface, similar to a contact lens, and the anterior surface can have a smooth convex curvature that is compatible with eye-lid motion.

Such body-mountable devices may include a variety of bio-interactive electronics disposed on as substrate that is substantially encapsulated in the polymeric material. For instance, the molding process may involve first forming a first layer of polymeric material, then positioning a substrate over the first layer, and then forming a second layer of polymeric material over the substrate and the first layer. The polymeric material can be cured and then removed from the molding form.

The electronics disposed on the substrate may include a sensor that is used to obtain measurements regarding the biological environment in which the body-mountable device is situated. For instance, an eye-mountable device may include an electrochemical sensor that is configured to obtain measurements of analyte concentration levels in tear fluid that coats the eye-mountable device. The electrochemical sensor includes electrodes disposed on the substrate which generate an amperometric current based on analyte concentrations when the electrodes are in fluid connection with a sample volume. Thus, to facilitate such measurements, the body-mountable device can include a channel through the polymeric material that exposes the sensor electrodes disposed on the embedded substrate.

A channel can be formed in the polymeric material using a protrusion in one of the molding forms to prevent polymeric material from forming over the sensor during molding. For example, after positioning the substrate over the first layer of polymeric material, the other part of the mold can be aligned with the protrusion extending to the sensor. The second layer of polymeric material can then be formed over the substrate and around the protrusion. Upon removing the cured polymeric material from the form, the polymeric material includes a channel that extends inward toward the sensor. The channel is shaped in accordance with the protrusion.

To prevent polymeric material from covering the sensor area during formation of the second layer, a sacrificial layer of conformal sealant material, such as polyethylene glycol, can be applied over the sensor before positioning the protrusion. The sacrificial sealant material covers the sensor and contacts both the sensor and the protrusion to fill gaps between the end of the protrusion and the sensor (e.g., due to machine tolerances in the depth of the substrate and/or sensor). When the protrusion is aligned and positioned in place, the sacrificial sealant material fills any tolerance gaps between the end of the protrusion and the sensor area on the substrate. The sacrificial sealant material thus provides a barrier against the polymeric material during formation of the second layer.

After final curing, the device can be removed from the mold and the sacrificial layer can be removed (e.g., by rinsing). Upon removing the sacrificial layer, the sensor electrodes can be exposed through the channel and the electrodes can be in fluid communication with an environment of the body-mountable device. In addition, the channel sidewalls are substantially defined by the protrusion, which allows the shape of the channel to be controlled and repeated.

It has also been found that the shape of the channel sidewalls can contribute to wearer comfort. For instance, in an eye-mountable device, wearer comfort may be determined in part by the degree of interference with eye-lid motion along the anterior surface of the device. Forming the channel by a protrusion machined in the anterior mold provides consistent, controllable profiles along the edges between the exterior surface and the channel sidewalls.

II. Example Body-Mountable Electronics Platform

FIG. 1 is a block diagram of a system 100 that includes a body-mountable device 110 in wireless communication with an external reader 180. The body-mountable device 110 is made of a polymeric material 120 formed to be mounted to a body surface. For instance, the polymeric material 120 may be formed to be contact-mounted to a corneal surface of an eye. A substrate 130 is embedded in the polymeric material 120 to provide a mounting location for electronic components such as a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the body-mountable device 110. The antenna 170, the controller 150, the power supply 140, and the bio-interactive electronics 160 can all be situated on the embedded substrate 130. In applications in which the body-mountable device is arranged to be contact-mounted to an eye, similar to a contact lens, it may also be referred to herein as an ophthalmic electronics platform.

A. Polymeric Material

The polymeric material 120 can be shaped to include an external surface that is configured to interface with a desired body-mounting location. For example, the polymeric material 120 may include a tooth-mountable surface, a head-mountable surface, an ear-mountable surface, a skin-mountable surface, an eye-mountable surface, and so on. The body-mountable device 110 may also be implemented in a form factor configured to be mounted to other body locations so as to access sample fluids in-vivo, including implantable configurations. For example, the polymeric material 120 may be smooth and include a bio-compatible coating suitable for applications in which the device 110 is implanted under and/or within the skin. The polymeric material 120 may partially or entirely encapsulate electronics within the device 110. In some examples, the body-mountable device 110 may include a mounting surface configured to be mounted to a tooth, a skin surface, a mucous membrane, upon a subcutaneous region, within an interstitial region, or in another region in which in-vivo fluid analyte concentrations may be measured.

To facilitate contact-mounting to an eye, the polymeric material 120 can have a concave surface configured to adhere ("mount") to a moistened corneal surface (e.g., by capillary forces with tear film coating the corneal surface). Additionally or alternatively, the body-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the body-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power (e.g., for vision correction applications).

B. Substrate

The substrate 130 includes one or more surfaces suitable for mounting the bio-interactive electronics 160, the controller 150, the power supply 140, and the antenna 170. The substrate 130 can be used both as a mounting platform for chip-based circuitry (e.g., by flip-chip mounting to conductive terminals patterned on the substrate 130) and/or as a platform for patterning conductive materials (e.g., gold, platinum, palladium, titanium, copper, aluminum, silver, metals, other conductive materials, combinations of these, etc.) to create electrodes, interconnects, connection pads, antenna, etc. In some examples, substantially transparent conductive materials (e.g., indium tin oxide) can be patterned on the substrate 130 to form circuitry, electrodes, etc. For example, the antenna 170 can be fabricated by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or electroplating techniques can be employed to pattern such materials on the substrate 130.

The substrate 130 can be a relatively rigid material, such as polyethylene terephthalate ("PET"), parylene, and/or another material configured to structurally support the circuitry and/or chip-based electronics within the polymeric material 120. The body-mountable device 110 can alternatively be arranged with a group of unconnected substrates rather than a single substrate. For example, the controller 150 and a sensor included in the bio-interactive electronics 160 can be mounted to one substrate, while the antenna 170 is mounted to another substrate and the two can be electrically connected via the interconnects 157. In another example, the substrate 130 can include separate partitions that each support separated, overlapped coiled portions of the antenna 170. Such as, for instance, an embodiment in which the antenna 170 is divided into multiple windings that wrap around the body-mountable device 110 circumferentially at respective radii, and are connected in parallel and/or in series. To facilitate movement of the individual windings with respect to one another, and thereby enhance flexibility of the body-mountable device 110, and help prevent binding or other deformation of the antenna, the individual windings may each be mounted on separated portions of the substrate 130.

In an eye-mountable application, the substrate 130 (and the bio-interactive electronics 160 thereon) can be positioned away from the area of the device 110 through which light is transmitted to the pupil (e.g., the center of the device). As such, the substrate 130 can avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some examples, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned so as to generate perceivable visual cues to a wearer of an eye-mountable device, such as by displaying information (e.g., characters, symbols, flashing patterns, etc.) on the pixel array 164.

The dimensions of the substrate 130 can depend on a variety of factors. For instance, in an eye-mountable application, the substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device. The substrate 130 can have a thickness sufficiently large to provide structural stability suitable for supporting the electronics mounted thereon. For example, the substrate 130 may be shaped as a ring with a diameter of about 10 millimeters, a radial width of about 1 millimeter (e.g., an outer radius 1 millimeter larger than an inner radius), and a thickness of about 50 micrometers. The substrate 130 may be shaped along the surface of an imaginary cone between two circular rings that define an inner radius and an outer radius. In such an example, the surface of the substrate 130 along the surface of the imaginary cone defines an inclined surface that is approximately aligned with the curvature of the eye mounting surface at that radius.

C. Power Supply

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from motion of the body-mountable device 110. The energy harvesting antenna 142 can optionally be a dual-purpose antenna that is also used to communicate information to the external reader 180. That is, the functions of the communication antenna 170 and the energy harvesting antenna 142 can be accomplished with the same physical component(s).

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage for powering the remaining electronics of the device 110 (e.g., the controller 150). In some cases, the power supply 140 may also include a rechargeable battery, such as a thin film solid state battery. Such a battery may be charged from the energy harvesting systems via the rectifier/regulator 144, and discharge to power the device 110 (e.g., during intervals when energy is not being harvested).

D. Controller and Bio-Interactive Electronics

The controller 150 can be turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the body-mountable device 110. For instance, one or more components, such as an analyte bio-sensor 162, can be used to obtain input from the biological environment. Additionally or alternatively, one or more components, such as pixel array 164, can be used to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction generates an amperometric current that can be measured through the working electrode. The amperometric current is related to the electrochemical reaction rate, which is related to the analyte concentration. Thus, the amperometric current that is measured through the working electrode can provide an indication of analyte concentration. In some embodiments, the sensor interface module 152 can be a potentiostat configured to apply a voltage between working and reference electrodes while measuring a current through the working electrode.

In some instances, a reagent can also be included to sensitize the electrochemical sensor to one or more particular analytes. For example, a layer of glucose oxidase ("GOx") proximal to the working electrode can catalyze glucose oxidation to generate hydrogen peroxide ($H_2O_2$). The hydrogen peroxide can then be electrooxidized at the working electrode, which releases electrons to the working electrode, resulting in an amperometric current that can be measured through the working electrode. These reactions are shown below.

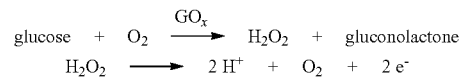

The current generated by either reduction or oxidation reactions is approximately proportionate to the electrochemical reaction rate. Further, the reaction rate is dependent on the rate of analyte molecules reaching the electrochemical sensor electrodes to fuel the reactions, either directly or catalytically through a reagent. In a steady state, analyte molecules diffuse to the electrochemical sensor electrodes at approximately the same rate that additional analyte molecules diffuse to the sampled region, and the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also be associated with one or more lenses to direct light to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the body-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the body-mountable device 110 can be arranged with one or more of the functional modules ("sub-systems") implemented in a single chip, integrated circuit, and/or physical component. For example, while the rectifier/regulator 144 is illustrated in the power supply block 140, the rectifier/regulator 144 can be implemented in a chip that also includes the logic elements of the controller 150 and/or other features of the embedded electronics in the body-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

E. Reader

The external reader 180 includes an antenna 188 (or a group of multiple antennas) to send and receive wireless signals 171 to and from the body-mountable device 110. The external reader 180 also includes a computing system with a processor 186 in communication with a memory 182. The memory 182 can be a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the body-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the body-mountable device 110 (e.g., sensor outputs from the analyte bio-sensor 162). The external reader 180 can also include one or more hardware components for operating the antenna 188 to send and receive the wireless signals 171 to and from the body-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earring, etc. or integrated in an article of clothing or an accessory worn near the head, such as a hat, headband, a scarf, a pair of eyeglasses, etc.

In some embodiments, the system 100 can operate to non-continuously ("intermittently") supply energy to the body-mountable device 110 to power the controller 150 and sensor electronics 160. For example, radio frequency radiation 171 can be supplied to power the body-mountable device 110 long enough to operate the sensor electronics 160 and communicate an outcome of such operation. In such an example, the supplied radio frequency radiation 171 can be considered an interrogation signal from the external reader 180 to the body-mountable device 110 to request feedback (e.g., a sensor measurement). By periodically interrogating the body-mountable device 110 (e.g., by supplying radio frequency radiation 171 to temporarily turn the device on), the external reader 180 can accumulate a set of measurements (or other feedback) over time from the sensor electronics 160 without continuously powering the body-mountable device 110.

F. Example Operation

In practice, the power supply 140 can function to harvest energy from received radio frequency radiation using the energy harvesting antenna 142 and the rectifier/regulator 146, and the harvested energy can be used to power the device 110. For example, radio frequency radiation can cause radio frequency electrical signals on leads of the antenna 142. The rectifier 146 can be connected to the antenna leads and convert the radio frequency electrical signals to a DC voltage, which can output supply voltages (i.e., the DC power 141) to operate the hardware logic of the controller 150 and also to power the electrochemical sensor 162. The DC supply voltage(s) 141 may be voltages suitable for driving digital logic circuitry, such as approximately 1.2 volts, approximately 3 volts, etc. In some examples, reception of the radio frequency radiation from the external reader 180 (or another source, such as ambient radiation, etc.) causes the supply voltages 141 to be supplied to the sensor 162 and hardware logic of the controller 150, thereby activating the body-mountable device 110. While powered, the sensor 162 and sensor interface 152 of the controller 150 are configured to generate and measure a current indicative of analyte concentration and communicate the results.

The external reader 180 associates the backscatter signal 171 with the sensor result (e.g., according to a pre-programmed relationship associating impedance of the antenna 170 with output from the sensor 162 using look-up tables, calibration information, etc.). The reader 180 can then store the indicated sensor results (e.g., analyte concentration values) in a local memory and/or an external data storage (e.g., by communicating through a network).

In some embodiments, one or more of the features shown as separate functional blocks can be implemented ("packaged") on a single chip. For example, the body-mountable device 110 can be implemented with a rectifier 144, voltage regulator, sensor interface 152, and other hardware logic packaged together in a single chip or controller module. The controller chip can also have interconnects ("leads") connected to the loop antenna 170 and the analyte bio-sensor 162 is disposed, which may be disposed on a sensor chip that is flip-chip mounted over conductive mounting pads, for example. Such a controller operates to harvest energy received at the loop antenna 170, apply a voltage between the electrodes of the sensor 162 sufficient to develop an amperometric current, measure the amperometric current, and indicate the measured current via the antenna 170 (e.g., through the backscatter radiation 171).

G. Example Eye-Mountable Electronics Platform

Figure 2A:
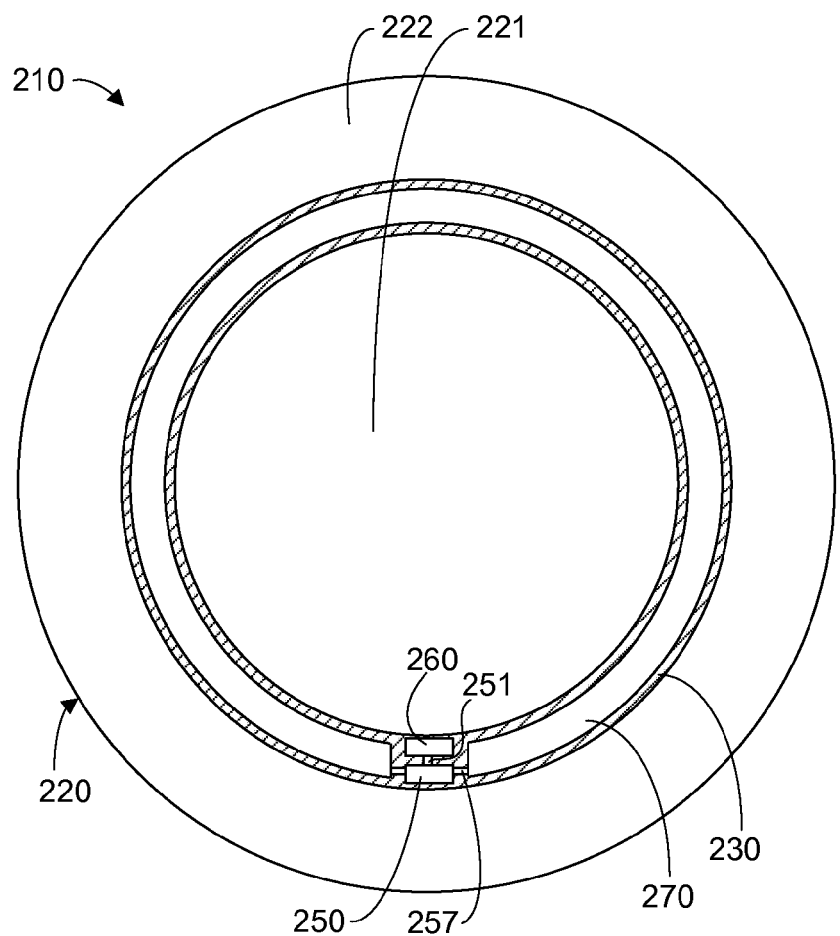
FIG. 2A is a top view of an eye-mountable device, according to an example embodiment.
Figure 2B:
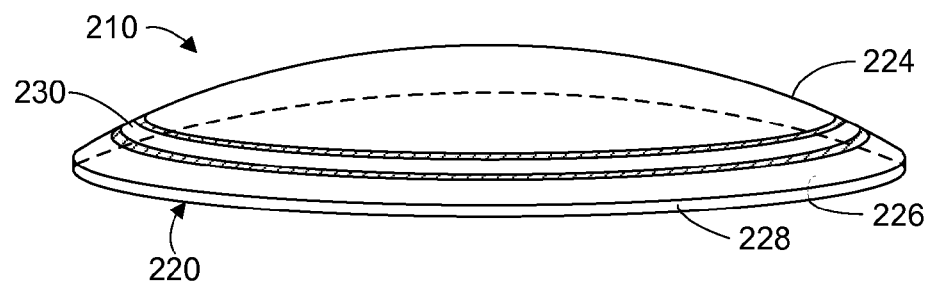
FIG. 2B is a side view of an eye-mountable device, according to an example embodiment.

FIG. 2A is a top view of an example eye-mountable device 210 (or ophthalmic electronics platform). FIG. 2B is an aspect view of the example eye-mountable device shown in FIG. 2A. It is noted that relative dimensions in FIGS. 2A and 2B are not necessarily to scale, but have been rendered for purposes of explanation only in describing the arrangement of the example device 210. The eye-mountable device 210 can be formed of a polymeric material 220 shaped as a curved disk. The eye-mountable device 210 includes a loop antenna 270, a controller 250, and an electrochemical sensor 260 mounted on a substrate 230 that is embedded in the polymeric material 220. The eye-mountable device 210 may use the electrochemical sensor 260 to obtain a measurement of analyte concentration in tear film surrounding the device 210.

The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("poly-HEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 226 and convex surface 224. The polymeric material 220 can be formed with a curved shape in a variety of ways. For example, techniques similar to those employed to form vision-correction contact lenses can be employed to form the polymeric material 220, such as heat molding, injection molding, spin casting, etc.

The eye-mountable device 210 can have dimensions similar to a vision correction and/or cosmetic contact lenses, such as a diameter of approximately 1 centimeter, and a thickness of about 0.1 to about 0.5 millimeters. However, these diameter and thickness values are provided for example purposes only. In some embodiments, the dimensions of the eye-mountable device 210 can be selected according to the size and/or shape of the corneal surface of the wearer's eye, to accommodate one or more components embedded in the polymeric material 220, and/or to achieve a target optical correction.

While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "top" view shown in FIG. 2A is an illustration facing the convex surface 224.

The substrate 230 can be embedded in the polymeric material 220 so as to be situated along the outer periphery 222 of the polymeric material 220, away from the central region 221. The substrate 230 can be shaped as a flat, circular ring (e.g., a disk with a central hole). The flat surface of the substrate 230 (e.g., along the radial width) serves as a platform for mounting electronics such as chips (e.g., via flip-chip mounting) and for patterning conductive materials (e.g., via microfabrication techniques such as photolithography, deposition, plating, etc.) to form electrodes, antenna (e), mounting pads, and/or interconnections. Both the substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented to assume a variety of different form factors, similar to the discussion of the substrate 130 in connection with FIG. 1 above.

The controller 250 can be a chip including logic elements configured to operate an electrochemical sensor and the loop antenna 270. The controller 250 is electrically connected to the loop antenna 270 by interconnects 257 also situated on the substrate 230. Similarly, the controller 250 is electrically connected to the sensor 260 by interconnects 251. The interconnects 251, 257, the loop antenna 270, and conductive electrodes included in the sensor 260 can be formed from conductive materials patterned on the substrate 230 by a process for precisely patterning such materials, such as deposition, photolithography, etc. In some instances, the electrochemical sensor 260 may include electrodes formed on a substrate separate from the substrate 230. Such a sensor chip may include bonding pads on the opposite side of the sensor chip to facilitate flip-chip bonding. For instance, the interconnects 251 that electrically couple the sensor 260 to the chip 250 may include traces that terminate with a pair of conductive mounting pads. The sensor 260 may then be flip-chip bonded over the mounting pads to thereby electrically couple the sensor 260 to the electronics in the chip 250. In other examples, the sensor electrodes may be patterned directly on the substrate 230 and the interconnects 251 may be traces that overlap each of the sensor electrodes. The conductive materials patterned on the substrate 230 can be, for example, gold, platinum, palladium, titanium, carbon, aluminum, copper, silver, silver-chloride, conductors formed from noble materials, metals, combinations of these, etc.

The loop antenna 270 is a layer of conductive material patterned along the flat surface of the substrate 230 to form a flat conductive ring. In some examples, to allow additional flexibility along the curvature of the polymeric material, the loop antenna 270 can include multiple substantially concentric sections electrically joined together in parallel or in series. Each section can then flex independently along the concave/convex curvature of the eye-mountable device 210. In some examples, the loop antenna 270 can be formed without making a complete loop. For instances, the antenna 270 can have a cutout to allow room for the controller 250 and the sensor 260, as illustrated in FIG. 2A. However, the loop antenna 270 can also be arranged as a continuous strip of conductive material that wraps entirely around the flat surface of the substrate 230 one or more times, and such strips can be connected in parallel and/or series to achieve desired signal performance. For example, a strip of conductive material with multiple windings can be patterned on the side of the substrate 230 opposite the controller 250 and sensor 260. Interconnects between the ends of such a wound antenna (e.g., the antenna leads) can then be passed through the substrate 230 to the controller 250.

Figure 2D:
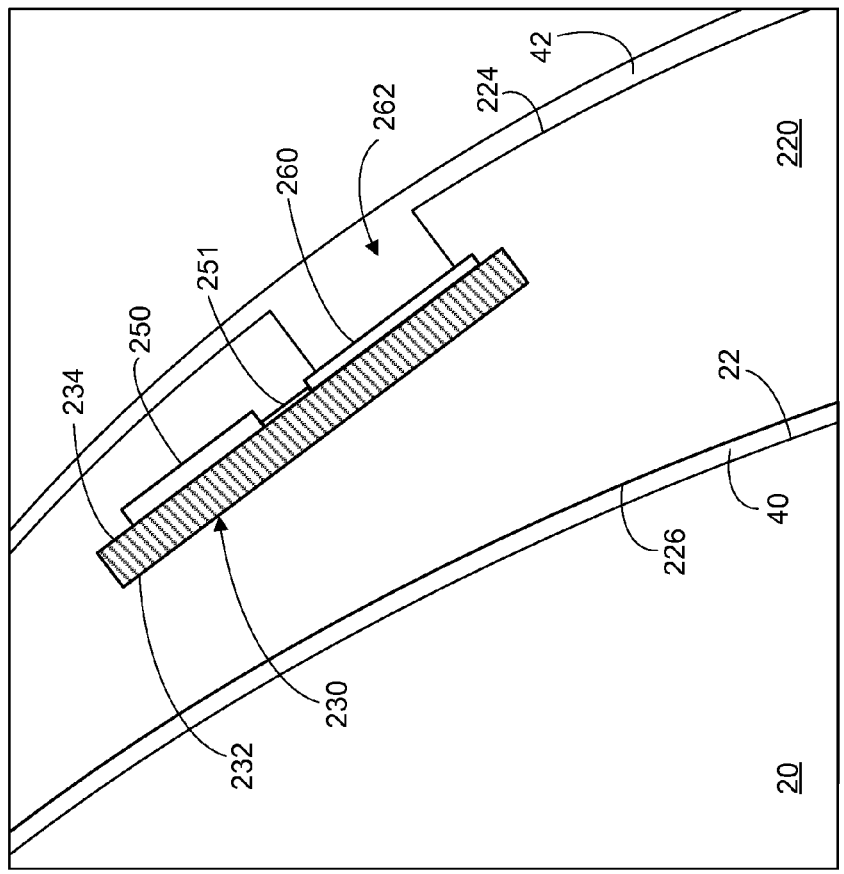
FIG. 2D is a side cross-section view showing the tear film layers surrounding surfaces of the eye-mountable device when mounted as shown in FIG. 2C, according to an example embodiment.
Figure 2C:
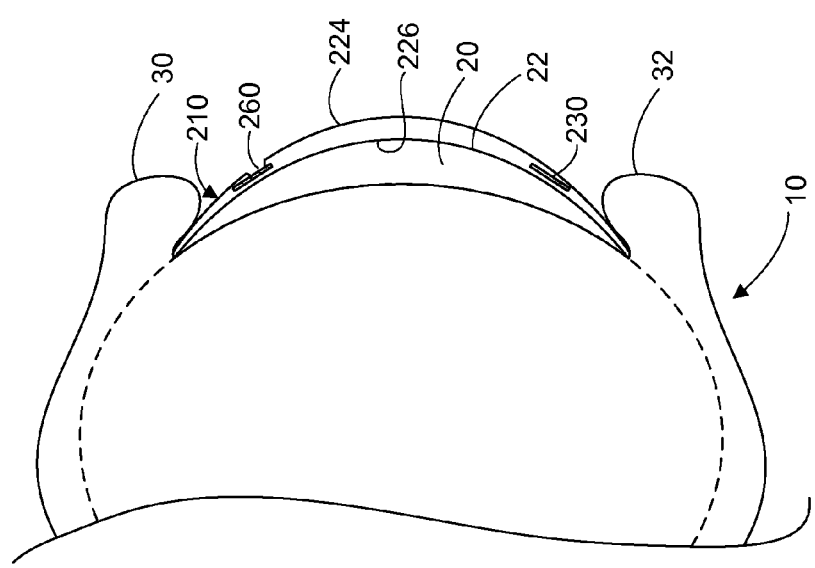
FIG. 2C is a side cross-section view of the eye-mountable device of FIGS. 2A and 2B while mounted to a corneal surface of an eye, according to an example embodiment.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 100-200 micrometers, while the thickness of the tear film layers 40, 42 can each be about 10 micrometers, although this ratio may not be reflected in the drawings. Some aspects are exaggerated to allow for illustration and to facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light-sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 5 to 10 micrometers in thickness and together account for about 5 to 10 microliters.

The tear film layers 40, 42 are distributed across the corneal surface 22 and/or the convex surface 224 by motion of the eyelids 30, 32. For example, the eyelids 30, 32 may raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22.

As shown in the cross-sectional views in FIGS. 2C and 2D, the substrate 230 can be situated such that the flat mounting surfaces of the substrate 230 are approximately parallel to an adjacent portion of the convex surface 224. The substrate 230 can be a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the electrochemical sensor 260, controller 250, and conductive interconnect 251 are mounted on the outward-facing surface 234. The electrochemical analyte sensor 260 may be disposed on the substrate 230 and electrically coupled to the controller 250 via the interconnect 251 patterned on the substrate 230. The controller 250 can use the electrochemical sensor 260 to obtain measurements of tear film analyte concentration by applying a voltage to electrodes of the electrochemical sensor 260 and monitoring the resulting amperometric current through the working electrode. The controller 250 can then use the antenna 270 to indicate the measured current. The eye-mountable device 210 may also include a channel 262 that exposes the sensor 260 to the outer tear film layer 42. The channel 262 can be an opening in the polymeric material 220 that is molded during fabrication of the eye-mountable device 210.

In some examples, other electronics, electrodes, etc. situated on the substrate 230 may be mounted to either the inward-facing side 232 or the outward-facing side 234. Moreover, in some embodiments, some electronic components can be mounted on one side (e.g., 232), while other electronic components are mounted to the opposing side (e.g., 234), and connections between the two sides can be made through conductive materials passing through the substrate 230.

The eye-mountable device 210 can be used to monitor the analyte concentration in tear film 40, 42 on the surface of the eye 10, as indicated by the sensor 260. The tear film 40, 42 is an aqueous layer secreted from the lacrimal gland to coat the eye 10. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, and other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

III. Example Channel Formation

Processes for forming body-mountable devices are disclosed herein. Some aspects relate to forming a channel in a body-mountable device. The channel can be positioned to expose a sensor in the device and thereby facilitate sampling of fluid to which the body-mountable device is exposed (e.g., blood, sweat, tear fluid, saliva). For example, body-mountable devices can be molded of a polymeric material that substantially encapsulates electronics disposed on a substrate. A channel can be formed in the polymeric material to expose a sensor disposed on the substrate. By exposing the sensor to bodily fluids, properties of those fluids can be measured and used to diagnose and/or monitor a health-related condition of the wearer. Example molding techniques for such devices may involve forming a first layer of polymeric material, positioning a substrate on the first layer, and forming a second layer of polymeric material over the substrate. The first and second layers of polymeric material can be combined together within the molding form to substantially encapsulate the substrate within the polymeric material. The molding form can shape the polymeric material in accordance with a cavity of the molding form.

The channel can be formed by a protrusion that extends from an inner molding surface of the molding form. For example, before forming the second layer of polymeric material over the substrate, the protrusion can be aligned with the sensor area and positioned to cover the sensor. A sacrificial sealant material can be applied to one or both of the sensor or end of the protrusion to seal the protrusion to the sensor. For example, the sealant material can fill any gaps between the sensor and the protrusion due to surface imperfections, fabrication tolerances, etc. While the sacrificial material contacts both the sensor and the protrusion, the second layer of polymeric material can be formed around the protrusion, thereby forming the channel to the sensor. The body-mountable device can then be removed from the molding form and the sacrificial material can be removed (e.g., by rinsing with a solvent). The resulting body-mountable device has a channel molded in the polymeric material to expose the sensor, and the channel is formed at least partially by the protrusion in the molding form.

In some examples, the fabrication process may also involve orienting the molding form with respect to the sensor before engaging the molding form. For example, the molding form may be a two-part apparatus, and the parts can engage one another at an interface that defines a boundary of a cavity within the molding form. The first layer of polymeric material and the substrate can be situated in the first part of the molding form, and the second part can be engaged with the first part before injection molding the second layer of polymeric material. Prior to engaging the two parts of the molding form, the second part can be oriented with respect of the substrate so as to align the protrusion with the sensor on the substrate. Orienting the protrusion can involve using an optical detection system to identify a location of the sensor on the substrate, and then manipulating the second part to cause the protrusion to be aligned with the identified location. Additionally or alternatively, orienting the protrusion can involve manipulating the substrate. For instance, the second part may be configured such that the protrusion engages the first part in a fixed location relative to the first part of the molding form. Thus, orienting the protrusion with respect to the substrate may involve manipulating the substrate until the sensor is at the fixed location.

The sacrificial sealant material can be applied to one or both of the protrusion and the sensor, and the molding form can be positioned such that the sealant material simultaneously contacts both the sensor and the protrusion. In some cases, a layer of sacrificial sealant material can be applied over the sensor before the substrate is positioned on the first layer of polymeric material. While the sensor is sealed by the sealant material, the second layer of polymeric material can be injection molded over the substrate and around the protrusion, which forms the channel. The polymeric material can be cured in the molding form, and then the resulting molded device can be removed from the molding form.

For purposes of illustration, fabrication processes are described herein in connection with a fabrication device that utilizes cast or compression molding, among other processes. It should be understood, however, that the disclosed channel fabrication processes may be carried out by a fabrication device that utilizes other methods and/or processes for forming body-mountable devices. In addition, fabrication processes are described herein in connection with fabrication of an eye-mountable device. It should be understood, however, that the processes may involve scenarios where the body-mountable device is another device configured to be mounted on or in other portions of a biological host. For example, the body-mountable device may comprise a tooth-mountable device and/or a skin-mountable device. Moreover, some applications may involve forming channels in molded devices to expose sensors therein in applications that do not involve mounting on or within a biological host.

FIGS. 3A, 3B, 3C, 3D, 3E, 3F, and 3G illustrate stages of forming an eye-mountable device using a molding system 300, according to an example embodiment. The molding system 300 includes a first part 310 and a second part 320. The first part 310 has a molding surface 312, and the second part 320 has a molding surface 322. The two parts 310, 320 are configured to engage one another at an interface 330. When so engaged, the two parts 310, 320 define a cavity 302 between the two molding surfaces 312, 322 and bounded by the interface 330. The cavity 302 is shaped to create an eye-mountable device therein. Thus, the cavity 302 may have a shape and dimensions similar to the eye-mountable device 210 described above in connection with FIGS. 2A-2D.

For example, the molding surface 312 can be a convex surface that defines a concave surface configured to be contact mounted to a corneal surface. Similarly, the molding surface 322 can be a concave surface that defines a convex surface configured to be positioned under the eyelids while the eye-mountable device is mounted to an eye. A protrusion 324 extends from the molding surface 322 of the second part to define a channel in the eye-mountable device. The concave surface of the eye-mountable device (defined by mounting surface 312) may also be referred to herein as a posterior surface. The convex surface of the eye-mountable device (defined by mounting surface 322) may also be referred to herein as an anterior surface.

Figure 3A:
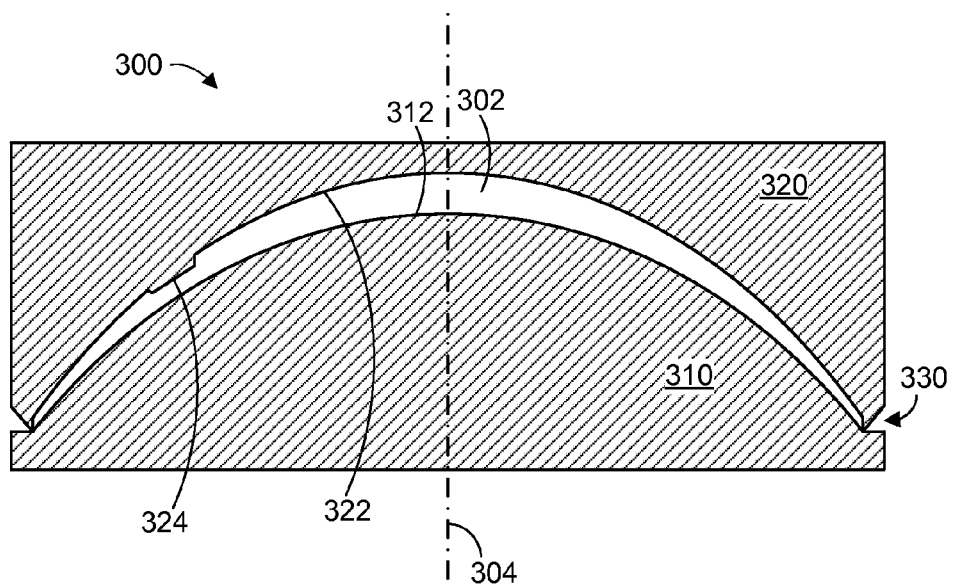
FIGS. 3A, 3B, 3C, 3D, 3E, 3F, and 3G illustrate stages of forming an eye-mountable device using a mold, according to an example embodiment.

The illustration in FIG. 3A shows a cross-sectional side view through the center of the molding system 300. FIG. 3A also shows a central axis 304, which can be an axis of symmetry of the molding system 300. For instance, the first part 310 can be cylindrically symmetric about the axis 304 such that the molding surface 312 is a convex surface that defines the posterior surface of the eye-mountable device. The second part 320 can also be substantially cylindrically symmetric, with the exception of the protrusion 324, which can occupy only a particular position on the molding surface 322 that corresponds to a location of a sensor in an eye-mountable device formed by the molding system 300. Moreover, the interface 330 at which the two parts 310, 320 engage one another can define a circular boundary of the eye-mountable device.

In some examples, the parts 310, 320 of the molding system 300 can be made of a metal, such as a stainless steel or other alloy, and/or plastic material, such as polyetherimide or another plastic with a high melting temperature. The molding surfaces 312, 322 may also include a non-stick coating such as polytetrafluoroethylene or another thermoplastic polymer. The molding surfaces 312, 322 may be configured to withstand curing temperatures of polymeric material molded therein, which may include a silicon hydrogel and/or other materials described above in connection with FIGS. 2A-2D. Further, in some examples, the molding system 300 may involve molding/curing processes that do not involve thermal curing. For instance, the molding system 300 may be used to mold polymeric materials that are cured by exposure to ultraviolet light or by application of another stimulus. In such examples, the molding surfaces 312, 322 may be configured to withstand exposure to ultraviolet light. As an example, the polymeric material molded between the molding surfaces 312, 322 may include polypropylene or polystyrene, which are cured by application of ultraviolet light.

Figure 3B:
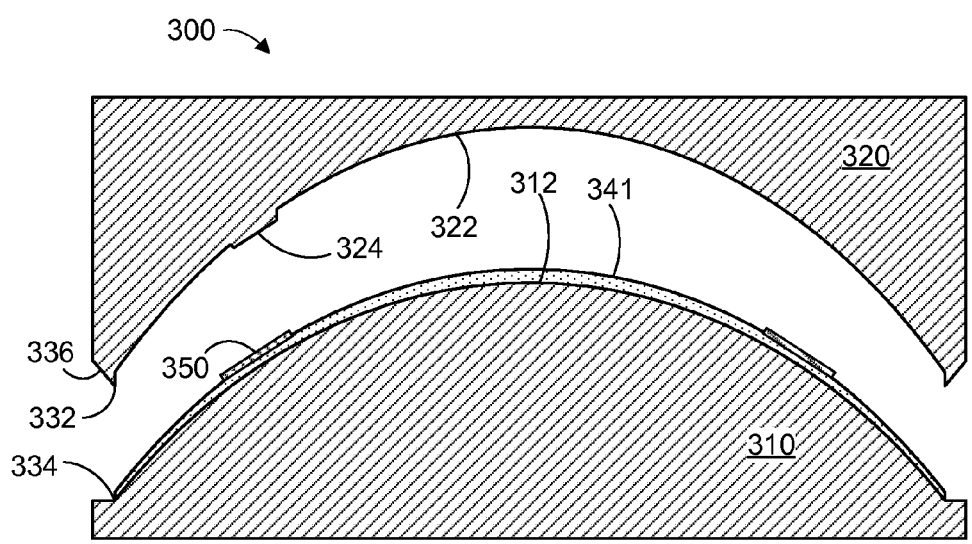

FIG. 3B shows the molding system 300 after forming a first layer of polymeric material 341 on the first part 310 and positioning a substrate 350 thereon. The first layer of polymeric material 341 may be formed over the molding surface 312 of the first part 310 by spin coating, injection molding, manual application, or another process. The first layer 341 can then be partially cured to allow the first layer 341 to hold its form and to support the substrate 350 when the substrate 350 is positioned thereon. The first layer 341 can be formed with a thickness of about 20-1000 micrometers, for example. As shown in FIG. 3B, the second part 320 of the molding system 300 can be disengaged from the first part 310 to make room for manipulating the substrate 350 over the first layer 341. The substrate 350 can include a sensor and various electronics disposed thereon, similar to the substrate 230 described in connection with FIGS. 2A-2D above. The substrate 350 can be a flattened ring and may be conformed to a curvature of the first layer of polymeric material 341 such that the mounting surface of the substrate 350 is approximately locally parallel to the unformed anterior surface of the eye-mountable device that corresponds to the molding surface 322.

As shown in FIG. 3B, the interface 330 between the first and second parts 310, 320 may be a pinch-off interface. The pinch-off interface includes a first interface 334, which can be a circular boundary of the molding surface 312, a sharpened interface 332, which can be a circular boundary of the molding surface 322, and a pinch-off cavity 336. The pinch-off cavity 336 can be a feature in the second part 320 (and/or the first part 310) that creates a cavity immediately adjacent the molding cavity 302 when the molding system 300 is engaged. The pinch-off cavity 336 receives excess polymeric material that does not fit in the cavity 302. The pinch-off interface can also provide a fine outer edge on the resulting eye-mountable device that does not interfere with eyelid motion when the device is mounted on an eye. In some examples, however, the interface 330 may be implemented without a pinch-off interface. For instance, some examples may involve an injection molding process in which polymeric material is injected from a port in one of the molding surfaces 312, 322 while the two parts 310, 320 remain engaged with one another.

Figure 3C:
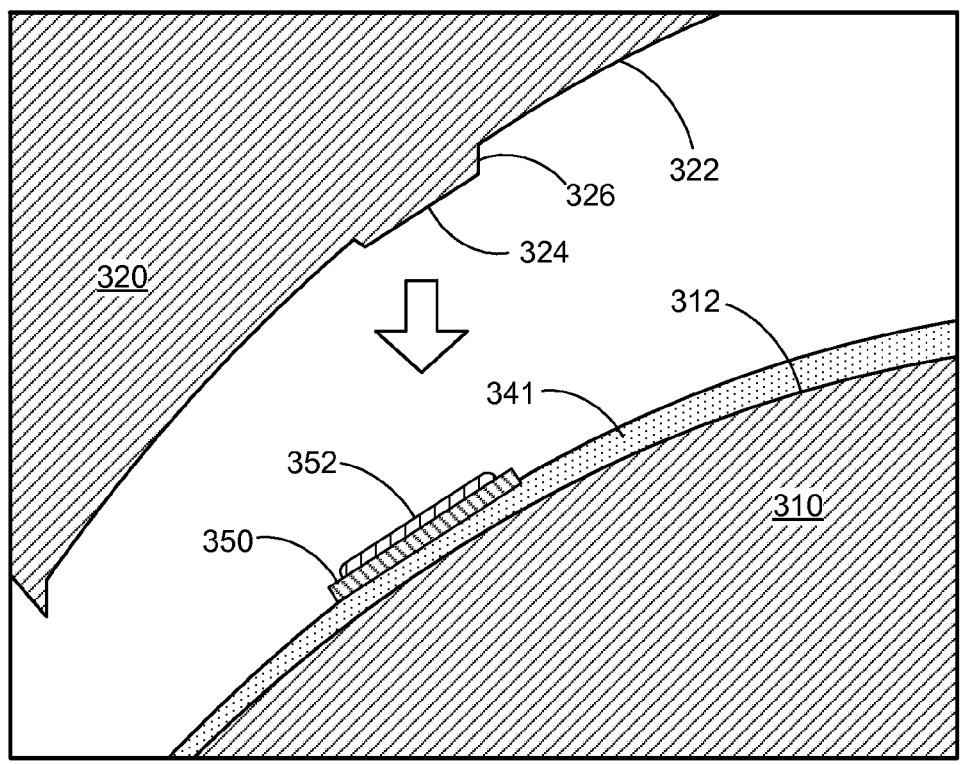

FIG. 3C is a close-in view of the cross-section shown in FIG. 3B. As shown in FIG. 3C, the substrate 350 can have a layer of sacrificial sealant material 352 disposed thereon. The sacrificial sealant material 352 can be applied with a thickness of about 20-100 micrometers and can substantially cover a sensor disposed on the substrate 350. The thickness of the sacrificial sealant material 352 may be based in part on manufacturing tolerances of the molding system, the geometry of the sensor, and the shape of the protrusion 324 that forms the channel. For instance, in some applications the thickness may be about 60-100 micrometers, while in other applications the thickness may be about 30 micrometers. Other examples are also possible. The sacrificial sealant material 352 may be polyethylene glycol (PEG) or another polymeric material, and may be applied by forming a drop over the sensor area after completing fabrication of the sensor. In some examples, the sensor can be an electrochemical sensor having at least two electrodes formed by metal material patterned and/or electroplated on the substrate 350. For example, an interdigitated pattern of palladium, platinum, gold, silver, or another metal can be patterned to form a working electrode and a reference electrode disposed on a sensor area of the substrate 350. The sacrificial sealant material 352 can then be applied over the sensor area to protect the electrodes formed in that area during any remaining fabrication processing of the substrate (e.g., mounting chips, patterning electrodes, applying biocompatible coatings, etc.). Thus, the sacrificial sealant material 352 may be applied in a thin layer while the sensor area is flat. Once applied, the sealant material 352 can be at least partially cured such that the sacrificial sealant material 352 holds its shape and position on the substrate 350 during further manipulation of the substrate 350. The substrate 350 (with sealant material 352 thereon) can then be positioned over the first layer 351 and conformed to the curvature thereof. In some examples, sacrificial sealant material may additionally or alternatively be applied to the protrusion 324.

As shown in FIG. 3C, the protrusion 324 extends from near the molding surface 322 to a distal end. The distal end can be a surface configured to engage the sensor area coated by the sacrificial sealant material 352. The view shown in FIG. 3C illustrates the second part 320 prior to engaging the first part 310. In some examples, the second part 320, the first part 310, and/or the substrate 350 may be manipulated so as to ensure that the protrusion 324 is aligned to contact the sacrificial sealant material 352 coating the sensor area on the substrate 350. Such alignment may include an optical detection system that images the substrate 350, identifies a location of the sensor area, and then causes a position and/or orientation of one or more components to be manipulated so as to align the protrusion 324 and the sensor area. Such alignment may also include, during the positioning and/or conforming of the substrate 350 on the first layer of polymeric material 341, aligning one or more fixed components on the substrate 350 with fixed components of the molding system 300. The alignment of the substrate 350 and such fixed components can be arranged such that the protrusion 324 is also aligned with the sensor area upon engaging the second part 320 with the first part 310. Other examples of aligning the protrusion 324 with the sensor area prior to engaging the molding parts 310, 320 are also possible.

The protrusion 324 also includes sidewalls 326 that can define sidewalls of the channel formed by the protrusion 324. The sidewalls 326 can be arranged such that opposing sidewalls generally become closer together closer to the distal end. Thus, a cross-sectional area of the protrusion 324 near the molding surface 322 can be greater than a cross-sectional area of the protrusion 324 at the distal end. In some cases, the sidewalls 326 can be arranged as portions of a conical surface with an apex further from the molding surface 322 than the distal end of the protrusion 324. Such a conical surface may have an opening angle between about 10° and about 80°, for example. Alternatively, the protrusion 324 (and the channel formed thereby) can have shapes other than conical portions. For instance, the protrusion 324 may have a cross sectional shape that is elliptical or rectangular with rounded edges, among other shapes. Moreover, the cross-sectional area of the protrusion 324 can gradually decrease toward the distal end. For example, the sidewalls 326 of the protrusion 324 may be inclined with respect to one another such that the span across the protrusion 324 (e.g., diameter of a circular/conical protrusion) is greater near the surface 322 than at the distal end.

The shape of the protrusion 324 may facilitate extraction of the protrusion 324 from the channel formed thereby during removal of the eye-mountable device from the molding system 300. In addition, the shape of the protrusion 324 may be configured to provide an edge profile on the resulting channel that enhances wearer comfort. For example, the protrusion 324 may form a transition between the channel and the exterior surface of the eye-mountable device to have a smooth edge (e.g., an angle between the sidewall and the exterior surface may exceed) 90°. Furthermore, so shaped, the channel can facilitate circulation and/or flushing of tear film throughout the channel, so as to increase accuracy of the sensor measurements. By contrast, if the channel is formed with overhanging polymeric material (e.g., due to a span of the channel near the sensor exceeding a span near the exterior surface), tear fluid may not readily circulate through the channel and the overhanging material could interfere with eyelid motion. The protrusion 324 can repeatedly and accurately form channels with sidewalls shaped in accordance with the sidewalls 326 of the protrusion 324.

Figure 3D:
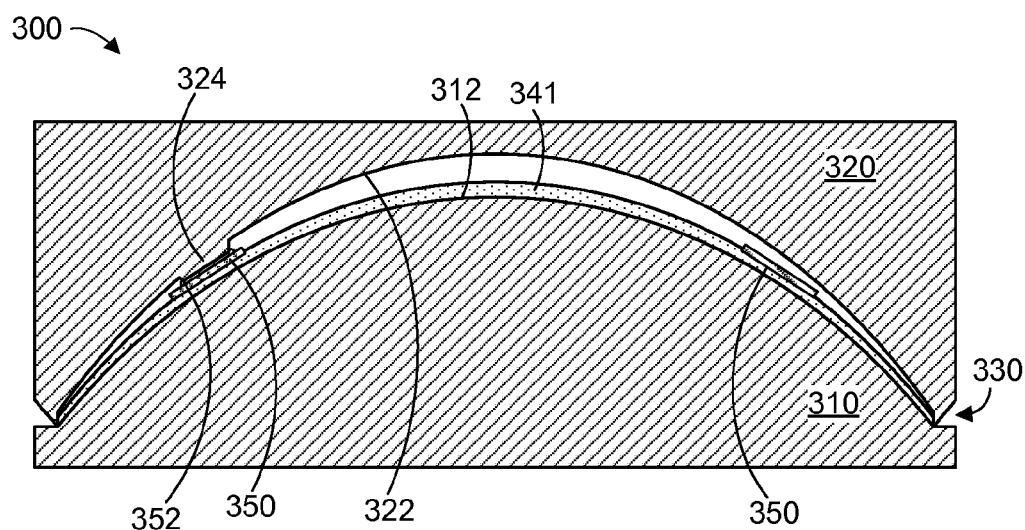

FIG. 3D shows the molding system 300 after the second part 320 engages the first part 310 at interface 330. The protrusion 324 makes contact with the sacrificial sealant material 352, which also contacts the sensor area of the substrate 350. The protrusion 324 and the sealant material 352 thereby jointly define a channel that will expose the sensor area upon formation of the remaining polymeric material. The sacrificial sealant material 352 fills spaces between the distal end of the protrusion 324 and the sensor area, which may be due to engineering tolerances, surface imperfections, and/or other factors. The protrusion 324 can therefore have a length that is approximately the depth of the resulting channel less the thickness of the layer of sacrificial sealant material 352. In some cases, the protrusion 324 may be configured to displace at least some of the sacrificial sealant material 352 during engagement of the second part 320, to thereby complete the seal. For instance, the sealant material 352 may have a thickness of about 40 micrometers, and the distal end of the protrusion 324 may be configured to penetrate to a depth of about 20 micrometers through the layer of sealant material. Such an example allows for a tolerance of plus or minus 20 micrometers in the placement of the protrusion 324 with respect to the sensor area during fabrication. Other examples are also possible.

In the event that some of the sealant material 352 is displaced by the protrusion 324 during engagement of the molding system 300, the displaced sealant material can be moved onto areas of the substrate 350 immediately adjacent the sensor area. After removing the sacrificial material, the displaced sealant material may also form a small lip at the base of the channel sidewalls, immediately adjacent the sensor. The remaining sidewalls of the channel can be formed in accordance with the shape of the protrusion 324.

Figure 3E:
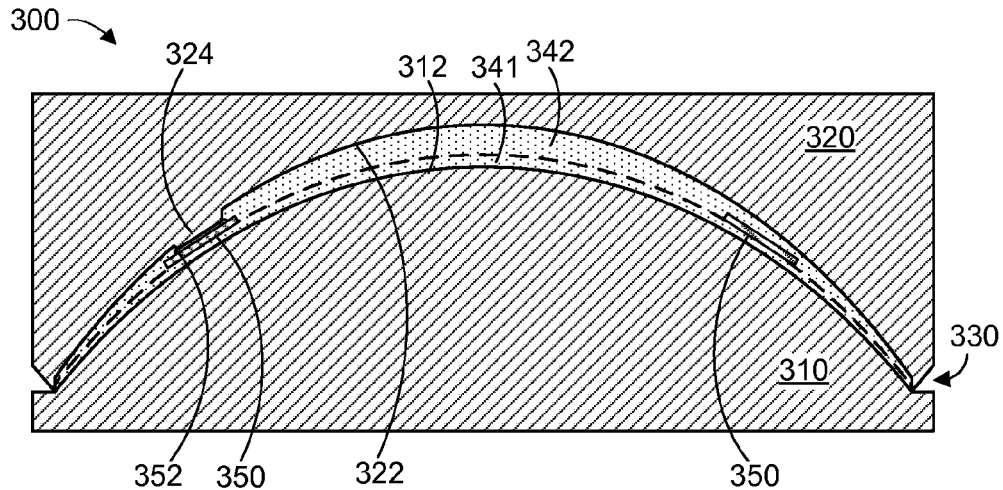

FIG. 3E shows the molding system 300 after forming the second layer of polymeric material 342. The second layer 342 is formed while the second part 320 is engaged with the first part 310 at the interface 330, and the while the sacrificial sealant material 352 is in contact with both the protrusion 324 and the sensor on the substrate 350. For example, polymeric material may be injected into the cavity of the molding system 300 (e.g., through an aperture in the molding surface 322 of the second part 320). The second layer of polymeric material 342 is formed over the substrate 350 and the first layer of polymeric material 341, and around the protrusion 324. The second layer 342 is also formed against the molding surface 322 of the second part 320. The first layer 341 and second layer 342 of the polymeric material together form an eye-mountable device. While the molding system 300 is engaged, the layers of polymeric material 341, 342 can be combined together and cured to create the molded eye-mountable device.

The protrusion 324 may be integrally formed with the second part 320 or can be attached to the molding surface 322 of the second part 320. For instance, the protrusion 324 may be machined into the molding surface 322 of the second part 320. In other examples, the protrusion 324 may be a separate component that is mechanically linked to the second part 320 of the molding system 300. For instance, the protrusion 324 may be implemented as a rod that extends through the second part 320. In such an example, the rod may be biased with a spring or another elastic device to allow the protrusion 324 to move in at least one direction with respect to the molding surface 322. Such a biased protrusion may be used, for example, to maintain contact with the sensor area via the sealant material 352 while the second part 320 is disengaged from the first part 310 of the molding system 300. The second part 320 and the first part 310 can then be engaged at the interface 330, which causes any excess polymeric material to be ejected at the pinch-off interface, and also forms a smooth outer edge of the resulting eye-mountable device.

Figure 3F:
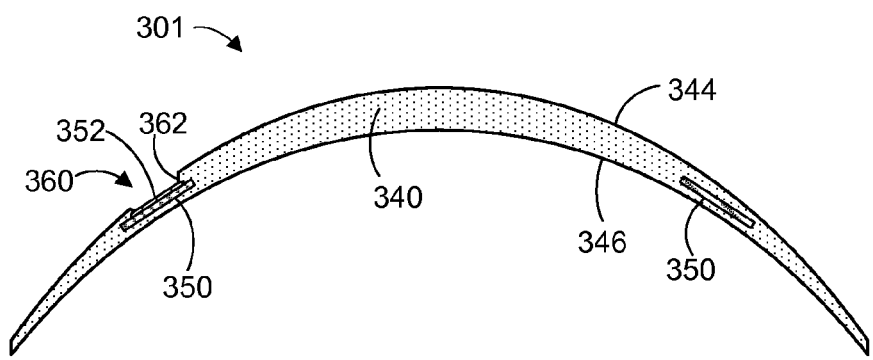

FIG. 3F shows an eye-mountable device 301 after being removed from the molding system 300. The eye-mountable device 301 can be removed by disengaging the first and second parts 310, 320 of the molding system 300 and extracting the eye-mountable device 301. The eye-mountable device 301 includes molded polymeric material 340 having a posterior surface 346 defined by the molding surface 312, an anterior surface 344 defined by the molding surface 322, and a channel 360 in the anterior surface 344 defined by the protrusion 324. The substrate 350 is substantially encapsulated within the polymeric material 340 aside from the channel 360 to the sensor. The channel 360 has sidewalls 362 that are shaped in accordance with the sidewalls 326 of the protrusion 324. The sensor area is covered by the sacrificial sealant material 352.

Figure 3G:
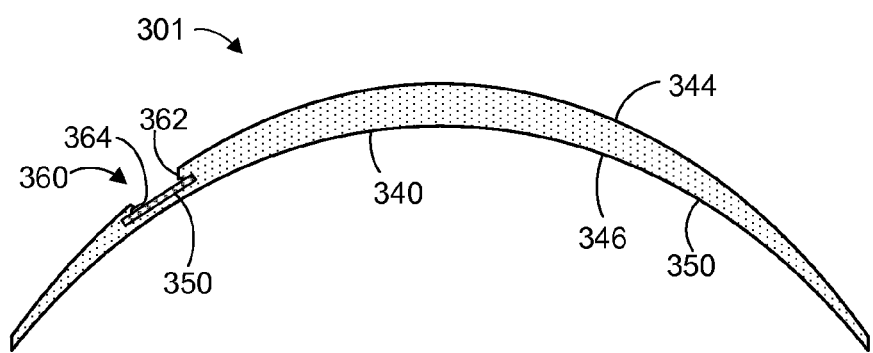

FIG. 3G shows the eye-mountable device 301 after removing the sacrificial sealant material 352 from the channel 360. The sacrificial sealant material 352 may be removed by rinsing the channel 360 with a solvent that dissolves the sacrificial sealant material 352. After removing the sealant material, the sensor 364 is exposed through the channel 360.

Figure 4:
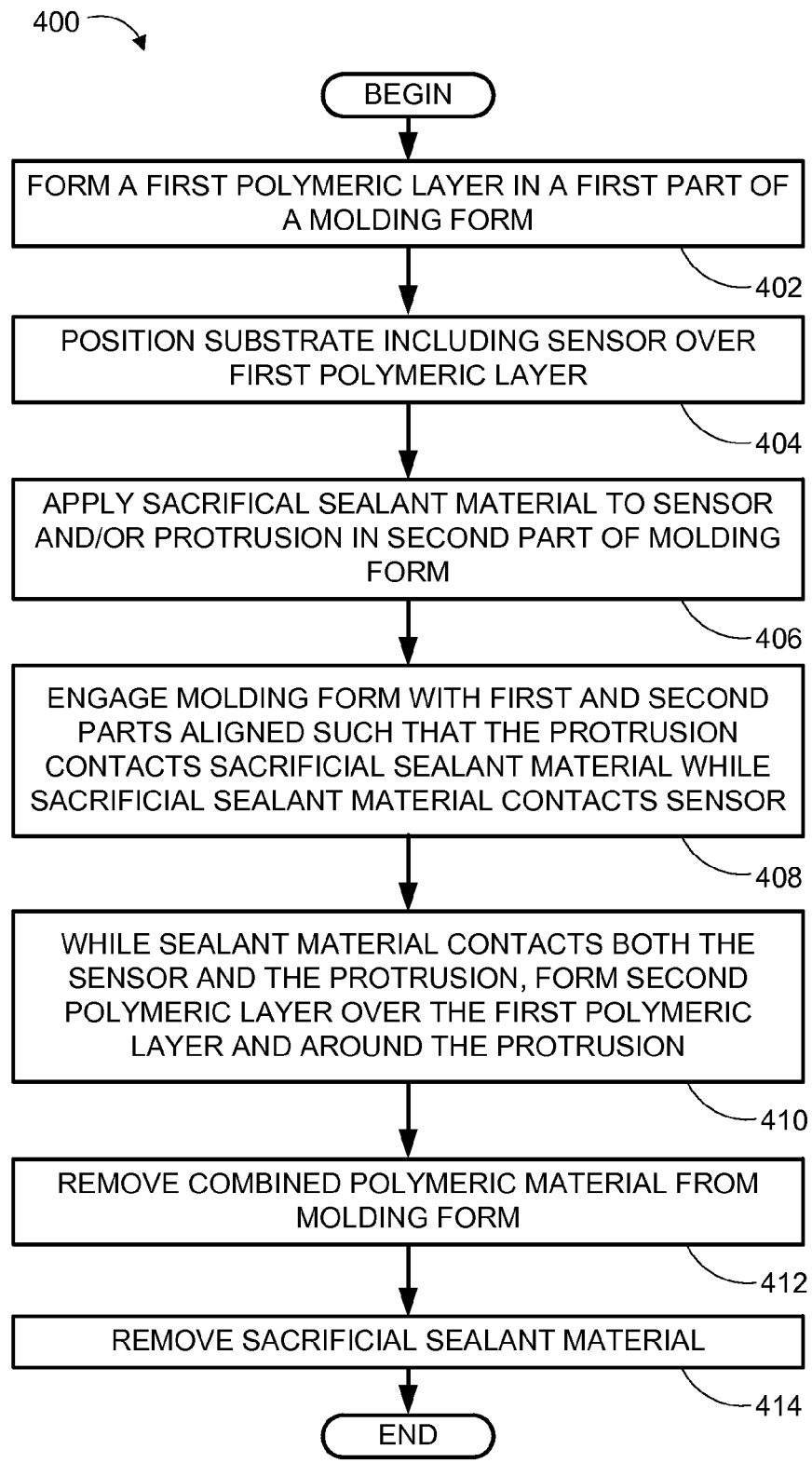
FIG. 4 is a flowchart illustrating a method of fabricating a body-mountable device, according to an example embodiment.

FIG. 4 is a flowchart illustrating a process 400 of fabricating a body-mountable device, according to an example embodiment. The process 400 may be carried out in whole or in part by an automated system, such as the molding system 300 described in connection with FIGS. 3A-3G. In some examples, the process 400 may be carried out by another molding system that is configured to fabricate another body-mountable or implantable device from polymeric material shaped in accordance with a mold. For example purposes, and to facilitate understanding, some techniques involved in the process 400 are described in reference to the fabrication of the eye-mountable device 301 using the molding system 300.

At block 402, the process 400 involves forming a first polymeric layer in a first part of a molding form. For example, the first layer of polymeric material 341 can be formed in the first part 310 of the molding system 300. The first layer 341 can be formed on the molding surface 312 of the first part 310. In some examples, the first polymeric layer can be partially cured to prevent the polymeric material from changing shape during subsequent fabrication processes.

At block 404, a substrate can be positioned over the first polymeric layer. The substrate can include a sensor disposed thereon as well as other electronics components, such as interconnects, an antenna, and a control chip configured to operate the sensor and the antenna to obtain measurements and communicate results. The substrate can be positioned by manipulating the substrate using a pick and place system or another manipulation system to place the substrate over the first polymeric layer. For example, the substrate 350 can be positioned over the first layer 341. As noted in connection with FIGS. 3B-3D, positioning the substrate 350 over the first layer 341 may involve aligning one or more features of the substrate with one or more features of the molding system. In some examples, an optical system may be used to capture image(s) of the substrate and/or molding system and identify locations of features (e.g., such as the sensor area) and then cause the substrate 350 and/or molding parts 310, 320 to move in a manner that effects alignment between the sensor and the protrusion 324 (once engaged).

At block 406, a sacrificial sealant material can be applied to the sensor area and/or the protrusion in the second part of the molding form. The application of the sealant material may be performed prior to forming the first polymeric material and positioning the substrate of blocks 402 and 404. For instance, the sacrificial sealant material may be applied to the sensor area during fabrication of the substrate and electronics thereon. The sealant material may be applied in a thin layer immediately over the sensor electrodes and at least partially cured to protect the sensor electrode during subsequent fabrication processes and/or manipulation of the substrate. In other examples, the sealant material may be applied using an applicator to spread the sealant material over the sensor area, or the sealant material may be sprayed or spin coated or dropped onto the sensor area. In some instances, the sacrificial sealant material is applied with a thickness between about 10 and 20 micrometers, although other thicknesses are also possible. The sacrificial sealant material may be polyethylene glycol (PEG) or another polymeric material that can be subsequently removed (e.g., by rinsing with a solvent that dissolves the sacrificial material).

At block 408, the molding form is engaged with the first and second parts aligned such that the protrusion contacts the sacrificial sealant material while the sacrificial sealant material also contacts the sensor. For example, when the two parts 310, 320 of the molding system 300 are engaged at the interface 330, the protrusion 324 from the molding surface 322 of the second part 320 contacts the sealant material 352, which also contacts the sensor area of the substrate 350, thereby sealing the sensor area. Engaging the molding form may involve orienting the two parts with respect to one another and then causing the two parts to move toward one another so as to engage one another.

At block 410, a second polymeric layer can be formed over the first polymeric layer and substrate and around the protrusion. During formation of the second polymeric layer, the sealant material maintains contact with both the sensor and the protrusion. The second polymeric layer forms around the protrusion and the sealant material sealed over the sensor inhibits the second polymeric layer from forming over the sensor. For example, the second layer 342 can be formed over the first layer 341 and around the protrusion 324, which is sealed to the sensor by the sealant material 352. The second layer of polymeric material 342 can then combine with the first layer 341 to form an eye-mountable device shaped in accordance with the cavity of the molding system 300. The shaped polymeric material can encapsulate the substrate 350 and electronics thereon with the exception of the sensor electrodes covered by the sealant material 352 and the protrusion 324. Combining the first and second layers of polymeric material within the molding form may involve curing the polymeric material.

At block 412, the shaped polymeric material can be removed from the molding form. The polymeric material extracted from the molding form can be shaped in accordance with the cavity of the molding form and can include at least one body-mountable surface. For example, the first part 310 and the second part 320 can be disengaged from one another and the shaped eye-mountable device 301 can be extracted from the molding system 300. Disengaging the two parts 310, 320 of the molding form 300 may involve moving the second part 320 away from the first part 310. Disengaging the molding form causes at least one of the molding surfaces 312, 322 to be released from the corresponding surfaces of the resulting eye-mountable device 301.

At block 414, the sacrificial sealant material can be removed from the channel. Removing the sacrificial sealant material exposes the sensor within the channel. For example, the sacrificial sealant material 352 can be dissolved from within the channel 360 by rinsing the eye-mountable device 301 with a solvent.

IV. Example Molded Channel

Figure 5A:
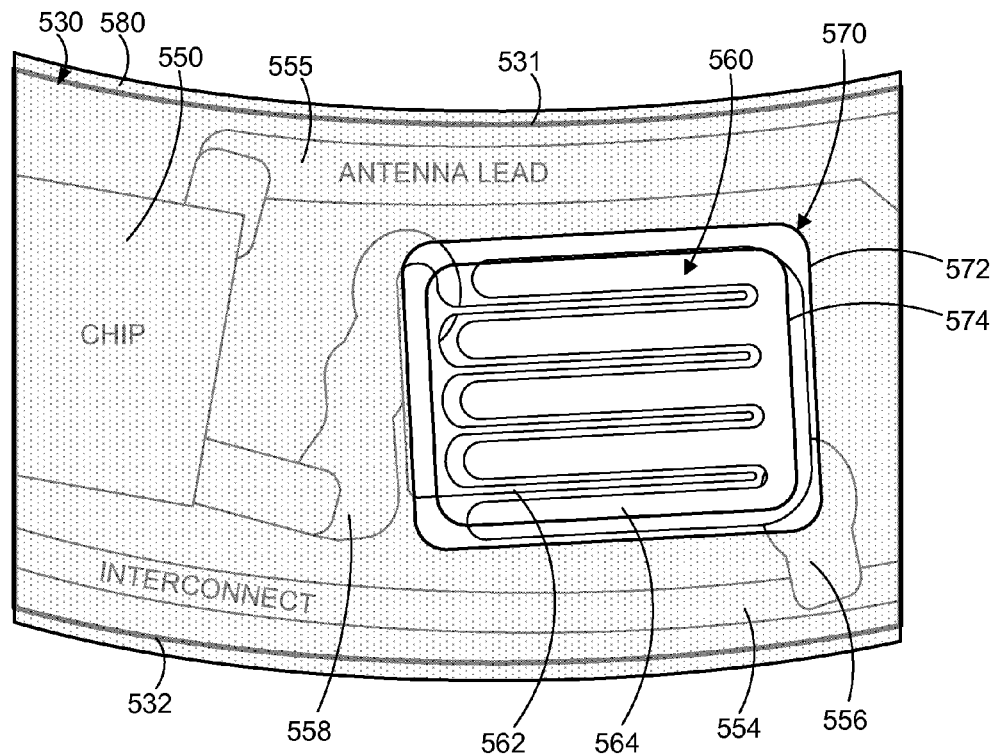
FIG. 5A is a top view of a channel that exposes a sensor area in an eye-mountable device, according to an example embodiment.
Figure 5B:
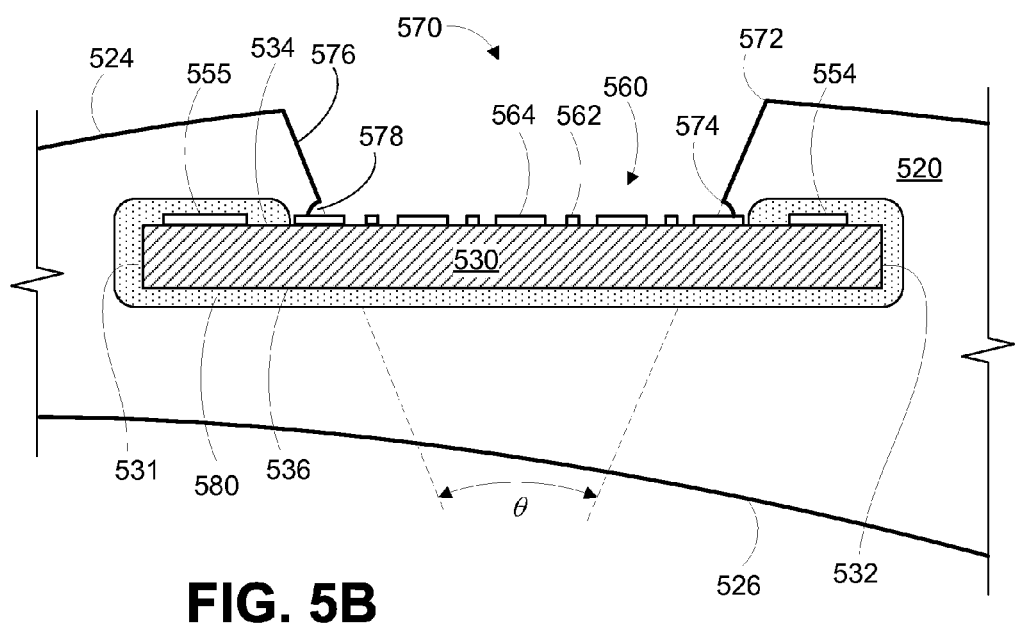
FIG. 5B is a side cross-sectional view of a channel that exposes a sensor area in an eye-mountable device, according to an example embodiment.

FIG. 5A is a top view of a channel 570 that exposes a sensor 560 in an eye-mountable device, according to an example embodiment. FIG. 5B is a side cross-sectional view of the channel 570. The sensor 560 is disposed on a substrate 530 embedded in an eye-mountable device. In addition to the sensor 560, the substrate 530 also includes a control chip 550 disposed thereon (e.g., mounted on conductive mounting pads patterned on the substrate 530). The control chip 550 can be connected to the sensor 560, an antenna, and other electronics on the substrate 530 by conductive traces patterned on the substrate 530.

The view in FIG. 5A illustrates a portion of the substrate 530. The substrate 530 may be a flattened ring suitable for embedding around a periphery of an eye-mountable device, for example. The substrate 530 includes an inner diameter 531 and an outer diameter 532. The substrate 530 also includes a mounting side 534 proximate an anterior surface 524 of the eye-mountable device and a reverse side 536 proximate a posterior side 526 of the eye-mountable device 526. FIG. 5A illustrates a view from the anterior side 524 looking through the transparent polymeric material 520 over the channel 570 formed therein to expose the sensor 560.

A conformal biocompatible material 580 encapsulates the substrate and electronics thereon, except for the sensor 560. The biocompatible coating 580 may be formed by parylene or another thermoplastic applied in a conformal layer over the substrate 530 and electronics thereon. For instance, the biocompatible coating 580 can cover the control chip 550 and the conductive traces disposed on the mounting side 534 of the substrate 530. In addition, the biocompatible coating 580 can cover the inner and outer diameter side edges 531, 532 and the reverse side 536 of the substrate 530. The sensor 560 can be uncovered due to a sacrificial layer covering the sensor 560 during application of the conformal biocompatible coating 580. In some applications, the biocompatible coating 580 may be omitted or applied to fewer locations.

The sensor 560 includes a pair of interdigitated electrodes 562, 564. The electrodes 562, 564 can be fabricated by patterning and/or electroplating conductive materials such as platinum, palladium, silver, gold, etc., in a desired pattern. The working electrode 562 can include a number of extensions with a width of approximately 25 micrometers that extend from an electrically connected base. Each of the extensions of the working electrode 562 can extend between respective extensions of the reference electrode 564. The reference electrode 564 can have extensions with a width of approximately 125 micrometers, for example, and each extension can extend from an electrically connected base. The extensions of the working electrode 562 can be approximately equidistant, along the side edges thereof, from extensions of the reference electrode 564 on both sides. During operation, a voltage applied between the electrodes 562, 564 induces electrochemical reactions to take place at the working electrode 562, preferentially along the side edges of the extensions thereof. A reagent may be localized on and/or around the sensor electrodes 562, 564 to sensitize the electrochemical sensor 560 to detection of a particular analyte. The electrochemical reaction rate, and thus analyte concentration, can be measured from an amperometric current through the working electrode 562. The respective bases of the electrodes 562, 564 provide electrical connection points for making interconnections with the control chip 550. For example, the control chip 550 can be electrically coupled to the working electrode 562 through an interconnection 558, and the control chip 550 can be electrically coupled to the reference electrode through a trace 554 and an interconnection 556. Moreover, the control chip 550 may be connected to an antenna through an interconnection 555.

The channel 570 that exposes the sensor electrodes 562, 564 can have a cross-sectional shape that corresponds to the area occupied by the two electrodes 562, 564 on the substrate 530. Thus, in FIG. 5A, the channel 570 has a generally rectangular shape with rounded corners. The channel 570 can have a span of approximately 200 micrometers to about 2 millimeters, depending on the dimensions of the sensor electrodes 562, 564. As used herein, the span of the channel 570 refers to a distance separating opposing sides of the channel 570. For example, a channel with a circular cross-section has a span which is a diameter of the circular cross-section. The channel 570 extends between the anterior surface 524 of the eye-mountable device and the sensor 560. The sidewalls 576 of the channel 570 extend between a top lip 572 and a bottom lip 574. The top lip 572 creates an edge between the exterior surface of the eye-mountable device (i.e., the anterior surface 524) and the sidewalls 576 of the channel 570. The transition defined by the top lip 572 can provide an angle greater than 90° between the exterior surface and the sidewalls 576, which may help mitigate interference with eyelid motion.

The channel 570 can also include a recess 578 formed by displaced sealant material that surrounds the protrusion during the molding process. For instance, when the protrusion contacts the sacrificial sealant material, some of the sealant material can be displaced to occupy a volume immediately adjacent the protrusion. After rinsing the eye-mountable device to dissolve the sacrificial sealant material, the displaced material can leave behind the recess 578. In some cases, the recess 578 may extend to partially uncover areas of the substrate 530 adjacent the sensor electrodes 562, 564. The bottom lip 574, which is formed by the distal end of the protrusion, can therefore overhang the recess. In some examples, the recess 578 may have a height less than 10 or 20 micrometers, whereas the channel 570 can have a depth into the polymeric material 520 that is about 100 micrometers or greater than 100 micrometers. The recess 578 is therefore a relatively small feature in the profile of the channel 570, which is predominantly defined by the protrusion that shapes the sidewalls 576.

As shown in FIG. 5B, the channel 570 can have a span that is greater near the exterior surface of the eye-mountable device (i.e., the anterior surface 524) than near the sensor. In other words, a distance across the channel 570 can be greater near the exterior surface than near the sensor 560. Opposing portions of the channel sidewalls 576 may be oriented with respect to one another along lines that intersect at a location further from the exterior surface than the sensor 560. For instance, in an example with a channel having a circular cross-section, the sidewalls of the channel may define a portion of a conical surface. The angle of intersection between opposing portions of the sidewalls 576 can be an angle $\theta$, as shown in FIG. 5B. The angle $\theta$ can be between about 10° and about 80°, for example. The relative orientation of the opposing sides of the sidewalls 576, and the shape of the channel 570 generally are defined by the protrusion in the molding form that shapes the eye-mountable device.

V. Additional Embodiments

It is noted that while the various electronics platforms are described herein by way of example as an eye-mountable device or an ophthalmic device, it is noted that the disclosed systems and techniques for configurations of sealed thin film batteries can be applied in other contexts as well. For example, contexts in which measurements are obtained in-vivo and/or from relatively small sample volumes, or are constrained to small form factors (e.g., implantable biosensors or other electronics platforms) may employ the channel formation processes described herein to form channels in such devices to expose interior portions thereof, such as sensor regions.

For example, in some embodiments, the electronics platform may include a body-mountable device, such as a tooth-mountable device. In some embodiments, the tooth-mountable device may take the form of or be similar in form to the body-mountable device 110 and/or the eye-mountable device 210. For instance, the tooth-mountable device may include a biocompatible polymeric material or a transparent polymer that is the same or similar to any of the polymeric materials or transparent polymers described herein and a substrate or a structure that is the same or similar to any of the substrates or structures described herein, although the exterior surface of the polymeric material may be formed to facilitate tooth-mounting, rather than eye-mounting. In such an arrangement, the tooth-mountable device may be configured to measure analyte concentration of a fluid (e.g., saliva) of a user wearing the tooth-mountable device. Other body mounting locations are also possible.

Moreover, in some embodiments, a body-mountable device may comprise a skin-mountable device. In some embodiments, the skin-mountable device may take the form of or be similar in form to the body-mountable device 110 and/or the eye-mountable device 210. For instance, the skin-mountable device may include a biocompatible polymeric material or a transparent polymer that is the same or similar to any of the polymeric materials or transparent polymers described herein and a substrate or a structure that is the same or similar to any of the substrates or structures described herein, although the exterior surface of the polymeric material may be formed to facilitate skin-mounting, rather than eye-mounting. In such an arrangement, the body-mountable device may be configured to measure analyte concentration of a fluid (e.g., perspiration, blood, etc.) of a user wearing the body-mountable device.

In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture. Such computing systems (and non-transitory computer-readable program instructions) can be configured according to at least some embodiments presented herein, including the processes shown and described in connection with FIG. 4.

The programming instructions can be, for example, computer executable and/or logic implemented instructions. In some examples, a computing device is configured to provide various operations, functions, or actions in response to the programming instructions conveyed to the computing device by one or more of the computer readable medium, the computer recordable medium, and/or the communications medium. The non-transitory computer readable medium can also be distributed among multiple data storage elements, which could be remotely located from each other. The computing device that executes some or all of the stored instructions can be a microfabrication controller, or another computing platform. Alternatively, the computing device that executes some or all of the stored instructions could be remotely located computer system, such as a server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The invention claimed is:

1. A system comprising:
a first molding part; and
a second molding part configured to engage the first molding part at an interface that defines a boundary of a cavity between the first molding and second molding parts,
wherein the cavity has a shape of an eye-mountable device,
wherein the first molding part comprises a first surface that defines a first portion of the cavity,
wherein the second molding part comprises a second surface that defines a second portion of the cavity and a protrusion that extends from a proximal end at the second surface and terminates at a distal end,
wherein the protrusion is disposed within the cavity,
wherein the protrusion comprises sidewalls,
wherein a first distance between the sidewalls at the proximal end is greater than a second distance between the sidewalls at the distal end, and
wherein the sidewalls define a portion of a conical surface with an opening angle between 10 degrees and 80 degrees.

2. The system of claim 1, wherein the distal end and proximal end have respective cross-sectional areas, and wherein the cross-sectional area of the proximal end is greater than the cross-sectional area of the distal end.

3. A body-mountable device comprising:
a polymeric material;
a substrate having a sensor disposed thereon, wherein the substrate is substantially encapsulated within the polymeric material; and
wherein the sensor is exposed through a channel in the polymeric material, wherein the channel extends between the sensor and an exterior surface of the body-mountable device, wherein the channel is bounded by sidewalls, wherein the channel comprises an edge between the exterior surface and one of the sidewalls, and wherein the edge provides an angle greater than 90 degrees between the exterior surface and the sidewall.

4. The body-mountable device of claim 3, wherein a first distance across the channel near the exterior surface is greater than a second distance across the channel near the sensor.

5. The body-mountable device of claim 3, wherein the polymeric material forms an eye-mountable device comprising a posterior surface configured to be removably mounted over an eye and an anterior surface configured to be compatible with eyelid motion when the posterior surface is so mounted, and wherein the channel forms an opening in the anterior surface.

6. The body-mountable device of claim 3, wherein the channel comprises a recess that extends from the sidewalls to expose a portion of the substrate adjacent the sensor.

* * * * *